United States Patent
Weigandt et al.

(10) Patent No.: US 10,561,733 B2
(45) Date of Patent: Feb. 18, 2020

(54) PROCESS FOR PRODUCING NANOPARTICLES LADEN WITH ACTIVE INGREDIENT

(71) Applicant: Merck Patent GmbH, Darmstadt (DE)

(72) Inventors: Markus Weigandt, Mannheim (DE); Senta Voss, Mainz (DE); Tobias Miller, Muenster (DE); Achim Goepferich, Sinzing (DE)

(73) Assignee: Merck Patent GmbH, Darmstadt (DE)

( * ) Notice: Subject to any disclaimer, the term of this patent is extended or adjusted under 35 U.S.C. 154(b) by 1083 days.

(21) Appl. No.: 14/380,989

(22) PCT Filed: Feb. 11, 2013

(86) PCT No.: PCT/EP2013/000396
§ 371 (c)(1),
(2) Date: Aug. 26, 2014

(87) PCT Pub. No.: WO2013/127490
PCT Pub. Date: Sep. 6, 2013

(65) Prior Publication Data
US 2015/0051181 A1    Feb. 19, 2015

(30) Foreign Application Priority Data

Feb. 29, 2012  (DE) .................. 10 2012 004 099

(51) Int. Cl.
| | | |
|---|---|---|
| *A61K 47/34* | (2017.01) | |
| *A61K 47/32* | (2006.01) | |
| *A61K 9/14* | (2006.01) | |
| *A61K 31/573* | (2006.01) | |
| *A61K 31/4375* | (2006.01) | |

(52) U.S. Cl.
CPC ............. *A61K 47/34* (2013.01); *A61K 9/14* (2013.01); *A61K 31/4375* (2013.01); *A61K 31/573* (2013.01); *A61K 47/32* (2013.01)

(58) Field of Classification Search
None
See application file for complete search history.

(56) References Cited

U.S. PATENT DOCUMENTS

2007/0122436 A1* 5/2007 Koltzenburg .......... A01N 25/04
424/405

OTHER PUBLICATIONS

Washington (International Journal of Pharmaceutics, 56 (1989) 71-74).*
International Search Report from PCT/EP2013/000396 dated Apr. 22, 2013.
Kevin Letchford et al. "A review of the formation and classification of amphiphilic block copolymer nanoparticulate structures: micelles, nanospheres, nanocapsules and polymersomes" European Journal of Pharmaceutics and Biopharmaceutics 65 (2007), pp. 259-269.
Alf Lamprecht et al. "Design of rolipram-loaded nanoparticles: comparison of two preparation methods" Journal of Controlled Release 71 (2001) pp. 297-306.
K. Elkharraz et al. "Paclitaxel-loaded microparticles and implants for the treatment of brain cancer: Preparation and physicochemical characterization" International Journal of Pharmaceutics 314 (2006) pp. 127-136.

* cited by examiner

*Primary Examiner* — David J Blanchard
*Assistant Examiner* — Garen Gotfredson
(74) *Attorney, Agent, or Firm* — Millen White Zelano and Branigan, PC

(57) ABSTRACT

The present invention relates to a novel process for the production of nanoparticles laden with active compounds and to the use thereof as medicaments. The process for the production of nanoparticles comprises the steps (a) dissolution of at least one active compound and at least one polymer in an organic solvent, (b) mixing of the solution prepared in step (a) with an aqueous phase, (c) evaporation of the organic solvent, (d) purification of the nanoparticles laden with active compound obtained in step (c) by means of dialysis against aqueous dialysis solution comprising the same active compound.

20 Claims, 3 Drawing Sheets

PROCESS FOR PRODUCING NANOPARTICLES LADEN WITH ACTIVE INGREDIENT

The present invention relates to a novel process for the production of nanoparticles laden with active compound(s), and to the use thereof as medicaments.

Nanoparticles are an innovative approach to the controlled release of pharmaceutical active compounds. In particular, polymer-based nanoparticles attracted considerable interest in recent decades. In these systems, the active compound(s) is (are) embedded in a polymer matrix and is (are) released in a controlled manner depending on the nature of the matrix. Essential advantages of such systems are: 1) increase in the solubility of hydrophobic active compounds, 2) reduction of undesired side effects through target-specific release, 3) control of the active compound pharmacokinetics by the active-compound carrier and 4) prevention of premature degradation of the active compounds after injection.

Due to the polymer content in the nanoparticles, the total amount necessary for therapeutic administration of the active compound is increased compared with administration of the active compound alone. Nanoparticles having the highest possible active-compound loading, i.e. the highest possible ratio of active compound to adjunct, are therefore desirable.

Adjuncts for medicaments must meet high requirements with respect to their physiological acceptability and quality, which have to be demonstrated to the responsible approval authorities in complex trials. The adjuncts used for the development of nanoparticles were and are therefore preferably adjuncts which have already been approved for use in medicaments. Examples of proven adjuncts which are suitable in nanoparticles are polylactic acid, polylactic acid-co-glycolic acid or polycaprolactone.

Disadvantageously, however, the proven adjuncts often do not exhibit pronounced compatibility with the active compound and therefore result in systems which can only be laden to a small extent.

One way of improving the adjunct/active compound compatibility is the use of novel polymers. Owing to the above-mentioned high requirements of such adjuncts, the development of nanoparticles comprising such (not yet approved) adjuncts is very time-consuming and expensive. In addition, the novel adjuncts are furthermore usually also not available in the quality required for medicaments (GMP quality).

Nanoparticles based on polymers can be produced using various processes. The production processes are:
1. Solvent Evaporation Methods
    a. Solvent/Non-Solvent Process (Also Known as O/W Emulsion Process)

Polymer and active compound are dissolved in a water-immiscible organic solvent, in particular dichloromethane, and introduced into an aqueous phase with constant agitation/stirring. The organic solvent is subsequently removed from the resultant emulsion either in vacuo or at atmospheric pressure (see, for example, V. P. Sant, D. Smith, and J. C. Leroux. Enhancement of oral bioavailability of poorly water-soluble drugs by poly(ethylene glycol)-block-poly(alkyl acrylate-co-methacrylic acid) self-assemblies. J Control Release. 104:289-300 (2005)). During this process, the laden nanoparticles are formed.

b. Multiple Emulsion Process (W/O/W Process)

W/O/W emulsion techniques are particularly suitable for the production of nanoparticles comprising somewhat hydrophilic and thus water-soluble active compounds. The polymer here is dissolved in a water-immiscible solvent (for example dichloromethane) and combined with an aqueous phase which comprises the dissolved active compound. The combined phases are homogenised (for example by stirring or ultrasound treatment), giving a W/O emulsion. The W/O emulsion is then injected into an aqueous phase which comprises an additional emulsifier as stabiliser. As the subsequent final step, the solvent is removed again in vacuo or under atmospheric pressure (K. Avgoustakis, A. Beletsi, Z. Panagi, P. Klepetsanis, A. G. Karydas, and D. S. Ithakissios. PLGA-mPEG nanoparticles of cisplatin: in vitro nanoparticle degradation, in vitro drug release and in vivo drug residence in blood properties; J Control Release. 79:123-135 (2002); C. X. Song, V. Labhasetwar, H. Murphy, X. Qu, W. R. Humphrey, R. J. Shebuski, and R. J. Levy. Formulation and characterization of biodegradable nanoparticles for intravascular local drug delivery. Journal of Controlled Release. 43:197-212 (1997)).

c. Co-Solvent Evaporation

In the method, active compound and polymer are mixed in an organic solvent and injected into the aqueous phase. The organic solvent is removed in vacuo or at atmospheric pressure. In contrast to the emulsion methods, the solvent used here is fully water-miscible, so that emulsions are not formed.

2. Dialysis
    a. Direct Dialysis

In the process, active compound and polymer are dissolved in a water-miscible organic solvent and introduced into a dialysis device. The dialysis can take place against water or buffer. The nanoparticles are produced by slow, constant exchange of the solvent following the concentration gradient of the internal and external phase. It remains noteworthy that, although the dialysis membranes used are permeable to small molecules (active compound), the polymer remains, however, in the internal phase owing to the exclusion sizes (H. J. Jeon, J. I. Jeong, M. K. Jang, Y. H. Park, and J. W. Nah. Effect of solvent on the preparation of surfactant-free poly(DL-lactide-co-glycolide) nanoparticles and norfloxacin release characteristics. International Journal of Pharmaceutics. 207:99-108 (2000)).

3. Film Hydration Methods

This process is a standard for the preparation of liposomal formulations. In it, the lipid or polymer is dissolved in an organic solvent and evaporated in vacuo. The film forming in the glass equipment is subsequently reconstituted with buffer, active-compound solution or water. It is disadvantageous that the resultant polymer/active-compound film may only be redispersible partly, if at all (A. Richter, C. Olbrich, M. Krause, J. Hoffmann, and T. Kissel. Polymeric micelles for parenteral delivery of Sagopilone: physicochemical characterization, novel formulation approaches and their toxicity assessment in vitro as well as in vivo. Eur J Pharm Biopharm. 75:80-89 (2010)). If the redispersion of the film does succeed, the process is usually followed, after production of the crude particles, by a step of size classification (membrane extrusion, ultrasound treatment) (E. Blanco, E. A. Bey, Y. Dong, B. D. Weinberg, D. M. Sutton, D. A. Boothman, and J. Gao. Beta-lapachone-containing PEG-PLA polymer micelles as novel nanotherapeutics against NQO1-overexpressing tumor cells. J Control Release. 122:365-374 (2007); Richter et al. in loco citato).

Production of nanoparticles with proven polymers by means of the processes described above often results in active-compound loading which is inadequate for therapeutic use thereof. It would be desirable to provide a process for the production of nanoparticles which, in spite of the adjunct/active compound compatibility problems arising here, allows the production of nanoparticles having high active-compound loading with conventional adjuncts.

Owing to the embedding of the active compound in the polymer, the known processes also result in nanoparticles from which the active compound is only released with a certain time delay (lag time). This has the consequence that therapeutic active-compound levels are only achieved with a time delay after administration of the nanoparticles, so that the additional administration of the active compound in a rapidly available form is necessary in order to achieve rapid onset of action.

Nanoparticles which release an amount of active compound immediately after administration, so that the active compound is already made available in therapeutic amount before the delayed release of active compound from the polymers, would therefore furthermore be desirable.

It was therefore an object of the present invention to provide a process for the production of nanoparticles that is not afflicted with the above-mentioned disadvantages of the existing production processes. The process should enable, in particular, the provision of nanoparticles which have higher active-compound loadings than nanoparticles produced using conventional processes and conventional polymers. Furthermore, the nanoparticles produced should already release an initial dose of the active compound immediately after their administration and thus result in prompt onset of action.

These objects have been achieved by a process for the production of nanoparticles that comprises the following steps: (a) dissolution of at least one active compound and at least one polymer in an organic solvent, (b) mixing of the solution prepared in step (a) with an aqueous phase, (c) evaporation of the organic solvent, (d) purification of the nanoparticles laden with active compound obtained in step (c) by means of dialysis against aqueous dialysis solution comprising the same active compound. The invention therefore relates to a process for the production of nanoparticles comprising the steps of (a) dissolution of at least one active compound and at least one polymer in an organic solvent, (b) mixing of the solution prepared in step (a) with an aqueous phase, (c) evaporation of the organic solvent, (d) purification of the nanoparticles laden with active compound obtained in step (c) by means of dialysis against aqueous dialysis solution comprising the same active compound.

The solution formed on dissolution of the active compound and the polymer in an organic solvent in step (a) is also called the organic phase above and below.

The aqueous phase employed can be water in which water-soluble substances, in particular salts, such as, for example, buffer salts, acids or bases, are dissolved. The mixing of the solution prepared in step (a) with the aqueous phase can be carried out by adding the solution prepared in step (a) to the aqueous phase or adding the aqueous phase to the solution prepared in step (a). Preference is given to the addition of the one solution to the other with constant stirring or shaking and optionally with use of ultrasound. Advantageously, the phase having the smaller volume is added to the phase having the larger volume during mixing, but the reverse process is also possible.

The aqueous phase consists of an aqueous solvent. An "aqueous solvent" in the sense of the invention is water, which may comprise substances dissolved therein, in particular, electrolytes, such as, for example, salts, acids or bases.

The removal of the organic solvent can be carried out by evaporation under standard conditions, i.e. at room temperature and atmospheric pressure, and can be accelerated by increasing the temperature and/or reducing the pressure, i.e. by reducing the pressure to a value below atmospheric pressure. The evaporation is preferably carried out at elevated temperature, particularly preferably at 30 to 60° C., and/or under reduced pressure, preferably at $10^{-4}$ to 80 mbar. The evaporation can advantageously be carried out, for example, using a rotary evaporator.

The dialysis can be carried out using conventional dialysis equipment known to the person skilled in the art, for example using a standard laboratory dialysis tube. The pore size of the dialysis membrane is advantageously selected so that the organic solvent and the active compound can pass freely through the dialysis membrane, but the polymer cannot. The upper exclusion weight (molecular weigh cutoff (MWCO)) of a suitable dialysis membrane is therefore preferably above the molecular weight of the active compound and of the solvent, but below the molecular weight of the smallest polymer molecules present in the polymer. For example, in the case of a lower molecular weight of the polymer of 15 kDa and a molecular weight of the active compound of, for example, 300 Da, a dialysis membrane having an MWCO below 5 kDa and above 1.5 kDa can be used. Dialysis membranes having an MWCO of 3.5 kDa or 5 kDa are usual and commercially available in this example.

If the dialysis solution comprises no active compound, the dialysis results in a reduction of active compound from the side comprising the nanoparticles owing to the concentration differences between the side comprising the nanoparticles and the side comprising the dialysis solution. As a consequence of the loss of active compound in the solvent surrounding the nanoparticles, a steep gradient in the concentration of active compound arises from the nanoparticles to this solvent, with the consequence that active compound is able to exit the nanoparticles and then passes over to the dialysis solution owing to the concentration gradient and is transported away. Due to the use according to the invention of dialysis solution in which the active compound is dissolved, this concentration gradient is at least reduced and thus counters the loss of active compound from the nanoparticles. The active compound may be present in the dialysis solution in all concentration to its maximum solubility (saturation solubility) in the dialysis solution, the dialysis solution is preferably saturated with active compound.

The active-compound loading of the nanoparticles may also drop due to diffusion and adhesion to the membranes employed. According to a preferred embodiment, the dialysis membrane is therefore brought into contact with dialysis solution comprising active compound, preferably with a dialysis solution saturated with active compound, before the dialysis is carried out, so that the membrane is enriched with active compound corresponding to the active-compound concentration present in the dialysis solution. According to a particularly preferred embodiment of the invention, the dialysis is carried out against dialysis solution saturated with active compound and with a dialysis membrane saturated with active compound.

As a consequence of the active compound present in the dialysis solution, the nanoparticles produced in accordance with the present process furthermore comprise an amount of active compound which is adsorbed at the nanoparticles. This active-compound content is advantageously available as initial dose immediately on administration to the patient.

According to an advantageous embodiment of the invention, the dialysis solution, besides the active compound, also comprises dissolved substances, in particular electrolytes, particularly preferably buffers and/or salts, which are also to be present in the formulation intended for the administration of the nanoparticles. Owing to liquid exchange, nanoparticles which are already present in a solvent which is suitable for administration to the patient are obtained in an advantageous and simple manner by this route as a consequence of the dialysis. Before administration to the patient, it is thus only necessary to ensure freedom from microbes, which can be carried out for example and in a simple manner by means of sterile filtration. Alternatively, the entire production process can also be carried out under aseptic conditions, so that subsequent sterilisation is not necessary.

After the dialysis, the nanoparticles are present in the aqueous solvent. If, as described above, the nanoparticles are obtained in a solvent which is suitable for administration to the patient, active compound dissolved in the solvent is also available as initial dose on administration to the patient, besides active compound adsorbed onto the nanoparticles.

If the aqueous solvent are removed from the nanoparticles, for example for stabilisation, which can preferably be carried out, for example, by means of freeze drying or also by means of spray drying, active compound dissolved in the solvent precipitates, at least in part, on the nanoparticles during the removal of water, so that this is likewise available as initial dose on administration to the patient.

In the process according to the invention, active compounds having a low saturation solubility in water, preferably having a saturation solubility <200 µg/ml, particularly preferably having a saturation solubility <100 µg/ml, are preferably employed (in each case measured at 25° C.). The invention therefore also relates to a process which is characterised in that the active compound has a saturation solubility in water <200 µg/ml, preferably a saturation solubility <100 µg/ml, in each case measured at 25° C.

Particularly preferred active compounds are active compounds selected from the group consisting of chemotherapeutic agents, in particular taxol derivatives, camptothecin derivatives, platinum complexes or N-mustard compounds, antirheumatics, such as, for example, glucocorticoids, in particular dexamethasone, mometasone, beclomethasone or prednisolone, anti-infective agents, such as, for example, HIV therapeutic agents, in particular ritonavir, and antimycotic agents, in particular ketoconazole, itraconazole, griseofulvin, lipid-lowering agents, such as, for example, fenofibrate, antioxidants and vitamins, such as, for example, tocopherol derivatives, retinoic acid derivatives, cholecalciferol, antibiotics, such as, for example, vancomycin or teicomycin, additionally cholesterol and fatty acids. The invention therefore furthermore relates to a process which is characterised in that the active compound used is an active compound which is selected from the group consisting of chemotherapeutic agents, in particular taxol derivatives, camptothecin derivatives, platinum complexes or N-mustard compounds, antirheumatics, such as, for example, glucocorticoids, in particular dexamethasone, mometasone, beclomethasone or prednisolone, anti-infective agents, such as, for example, HIV therapeutic agents, in particular ritonavir, and antimycotic agents, in particular ketoconazole, itraconazole, griseofulvin, lipid-lowering agents, such as, for example, fenofibrate, antioxidants and vitamins, such as, for example, tocopherol derivatives, retinoic acid derivatives, cholecalciferol, antibiotics, such as, for example, vancomycin or teicomycin, additionally cholesterol and fatty acids.

According to an advantageous embodiment of the invention, the polymer employed in the process is an amphiphilic polymer. The invention therefore also relates to the process according to the invention which is characterised in that the polymer employed is an amphiphilic polymer. Amphiphilic polymers are built up from a hydrophilic ("water-loving") and a hydrophobic ("water-hating") parts. Owing to this structure, amphiphilic polymers preferentially accumulate at the interfaces between the aqueous and the organic phase in heterogeneous mixtures comprising water and water-immiscible solvents, in particular organic solvents, such as, for example, dichloromethane.

According to a particularly advantageous embodiment of the invention, the amphiphilic polymers used are block copolymers. The invention therefore also relates to a process which is characterised in that the polymer employed is a block copolymer. Block copolymers consist of one or more, also different blocks comprising a hydrophilic component a) and a hydrophobic component b), where the individual blocks may contain identical monomers having identical or different chain length or different monomers. Components a) and b) may be simultaneously or independently of one another linear or branched, comb- or star-shaped. Component b) may also be a crosslinked polymer.

Particularly suitable as hydrophobic component b) are biodegradable polymers, such as, for example, polyester, poly-ε-caprolactone, poly-α-hydroxyester, poly-β-hydroxyester, polyanhydride, polyamide, polyphospazene, polydioxanone, polymalic acid, polytartaric acid, polyorthoester, polycarbonate, polysaccharide, peptide and protein.

As hydrophilic component a) is built up from at least bifunctional and preferably water-soluble building blocks, examples of suitable polymers are polyethylene glycols, polyacrylamides, polyvinyl alcohol, polysaccharides (for example modified celluloses and starches), alginates, peptides and proteins.

Block copolymers which can be employed in accordance with the invention may contain as hydrophilic component, for example, polyethylene glycol, polypropylene glycol, polybutylene glycol, polyacrylamide, polyvinyl alcohol, polysaccharide or a copolymer thereof, preferably polyethylene glycol-polypropylene glycol copolymer, polyethylene glycol-polypropylene glycol-polyethylene glycol copolymer, and as hydrophobic component polylactic acid, polyglycolic acid, polyhydroxybutyric acid, polyhydroxyvaleric acid, or a copolymer thereof, preferably polylactic-co-glycolic acid, furthermore polyacrylic acid and derivatives thereof, in particular hydroxypropylethylacrylic acid or hydroxypropylmethylacrylic acid, polysiloxane and derivatives thereof, in particular copolymers with acrylic acid, polystyrene or a copolymer thereof, in particular with polylactic acid and polyglycolic acid. The invention therefore also relates to a process which is characterised in that the block copolymer contains as hydrophilic component polyethylene glycol, polypropylene glycol, polybutylene glycol, polyacrylamide, polyvinyl alcohol, polysaccharide or a copolymer thereof, preferably polyethylene glycol-polypropylene glycol copolymer, polyethylene glycol-polypropylene glycol-polyethylene glycol copolymer, and as hydrophobic component polylactic acid, polyglycolic acid, polyhydroxybutyric acid, polyhydroxyvaleric acid, or a copolymer thereof, preferably polylactic-co-glycolic acid, furthermore polyacrylic acid and derivatives thereof, in particular hydroxypropylethylacrylic acid or hydroxypropylmethylacrylic acid, polysiloxane and derivatives thereof, in particular copolymers with acrylic acid, polystyrene or a copolymer thereof, in particular with polylactic acid and polyglycolic acid.

According to an advantageous embodiment of the invention, the block copolymers employed are polyethylene glycol-polylactic acid, polyethylene glycol-polyglycolic acid, polyethylene glycol-polylactic acid co-glycolic acid, polyethylene glycol-polyhydroxyvaleric acid, polyethylene glycol-polysiloxane, polyethylene glycol-polysiloxane-co-acrylic acid, polyethylene glycol-polymethylmethacrylic acid, polyethylene glycol-polymethylethacrylic acid, polyethylene glycol-polyisoprylacrylic acid, polyethylene glycol-polystyrene. The invention therefore also relates to a process which is characterised in that the block copolymers employed is polyethylene glycol-polylactic acid, polyethylene glycol-polyglycolic acid, polyethylene glycol-polylactic acid-co-glycolic acid, polyethylene glycol-polyhydroxyvaleric acid, polyethylene glycol-polysiloxane, polyethylene glycol-polysiloxane-co-acrylic acid, polyethylene glycol-polymethylmethacrylic acid, polyethylene glycol-polymethylethacrylic acid, polyethylene glycol-polyisoprylacrylic acid, polyethylene glycol-polystyrene.

According to a further advantageous embodiment, the organic solvent employed in the process according to the invention is a solvent which is at least partially miscible, preferably fully miscible, with water. The invention therefore also relates to a process which is characterised in that the organic solvent used is a solvent which is at least partially miscible, preferably fully miscible, with water.

For the purposes of the invention, a solvent which is at least partially miscible with water is a solvent with which water can be admixed in a volume ratio of at least 40/60 v/v (organic solvent/water) at room temperature (25° C.) to give a uniform, homogeneous phase. If the maximum proportion of water that can be admixed is exceeded to give a homogeneous phase, phase separation occurs between the homogeneous organic and water-containing first phase and a second phase consisting of water. An organic solvent which is fully miscible with water is an organic solvent with which water can be admixed in any volume ratio at room temperature (25° C.) to give a uniform, homogeneous phase.

Organic solvents which can be employed in the process according to the invention are linear or branched-chain alcohols, preferably methanol, ethanol, isopropanol, n-butanol or tert-butanol, acetone, dimethylformamide, tetrahydrofuran or dimethyl sulfoxide. The invention therefore also relates to a process which is characterised in that the organic solvent employed is linear or branched-chain alcohols, preferably methanol, ethanol, isopropanol, n-butanol or tert-butanol, acetone, dimethylformamide, tetrahydrofuran or dimethyl sulfoxide.

Active compounds which are acids or bases can in accordance with the invention preferably be mixed, in each case in a complementary manner, with a base or acid in order to increase their solubility. If the active compound is an acid a base is thus added thereto, if it is a base an acid is added. The acid or base can be added in step (a) or in step (b) in the process according to Claim 1. The invention therefore also relates to an embodiment of the process according to the invention which is characterised in that, in step (a) according to Claim 1, an acid or base is dissolved in the organic solvent besides polymer and active compound, and/or in that an acid or base is dissolved in the aqueous solvent in step (b) of Claim 1.

Suitable acids are organic acids, preferably formic acid, acetic acid or trifluoroacetic acid, or inorganic acids, preferably hydrochloric acid, nitric acid or sulfuric acid, suitable bases are organic bases, preferably dimethylamine or trimethylamine, or inorganic bases, preferably sodium hydroxide, potassium hydroxide or ammonia. The invention therefore also relates to a process which is characterised in that the acid is an organic acid, preferably formic acid, acetic acid or trifluoroacetic acid, or an inorganic acid, preferably hydrochloric acid, nitric acid or sulfuric acid, and the base is an organic base, preferably dimethylamine or trimethylamine, or an inorganic base, preferably sodium hydroxide, potassium hydroxide or ammonia.

According to an advantageous embodiment of the process according to the invention, the organic solvent employed for the dissolution of active compound and polymer is selected as described below. In each case here, a defined amount of the active compound which is to be embedded in the formulation is added and dissolved in a selection of solvents which are at least partially miscible with water. According to an advantageous embodiment of the invention, the selection of solvents includes, for example, alcohols (methanol, ethanol, isopropanol, 1-propanol, tert-butanol), dimethyl sulfoxide (DMSO), dimethylformamide (DMF), dioxane, tetrahydrofuran (THF), acetonitrile (ACN) and acetone. If the active compound is an acid or base, an acid or base is in each case preferably added thereto in accordance with the procedure described above.

For the solution, in each case equal amounts of active compound are dissolved in in each case equal amounts of organic solvents. The amount of active compound and organic solvent which is employed in each case is variable, the crucial factor is that the ratio of active compound to solvent is the same in each case. For practical implementation, it has proven advantageous to dissolve in each case 1 mg of active compound in 100 µl of organic solvent.

If the active compound is insoluble in an organic solvent, this solvent is less suitable for the production of nanoparticles. If a clear solution is formed, in each case equal defined amounts of aqueous solvent are added stepwise and mixed in each case until precipitation of the active compound is visible after addition and mixing (visual solubility). The assessment of visual solubility is carried out visually in a suitable container, preferably in a glass tube having a small diameter, for example as are customary in gas chromatography (diameter of 0.5 cm, height 3 cm), under cold light, which preferably radiates upward, against a dark surface, preferably against a black surface, as background. A diagrammatic representation of the procedure is depicted in FIG. 1.

According to a preferred embodiment of the invention, the aqueous solvent employed is an aqueous solvent that the same composition as the aqueous solvent used in the process in step (b) according to Claim 1.

The organic solvent with which the greatest proportion of aqueous solvent can be admixed without the active compound precipitating out of the solution is particularly suitable for use in the process according to the invention. The present invention therefore also relates to an embodiment of the process that is characterised in that the organic solvent used in the production of the nanoparticles in step (a) of Claim 1 is the organic solvent with which the greatest proportion of aqueous solvent can be admixed without the active compound precipitating out of the solution during preparation of a solution comprising the active compound in defined amount compared with solutions comprising this active compound in the same amount in each case in other organic solvents on successive admixing of aqueous solvent.

Use of an organic solvent with which the greatest proportion of aqueous solvent can be admixed on successive admixing of aqueous solvent enables it to be ensured that active compound and polymer remain in solution for longer during evaporation of the organic solvent in step (c) of Claim 1, compared with the use of other solvents.

The evaporation of the organic solvent in step (c) according to Claim 1 from the solvent mixture prepared in step (b) results, as a consequence of the reduction of the proportion of organic solvent in the solvent mixture, in a continuous reduction of the solubility of active compound and polymer in the solvent mixture. If inadequate solubility for the active compound arises for an organic solvent in a mixture with the aqueous solvent during evaporation in the case of only a slight reduction in its proportion in the solvent mixture, the active compound already precipitates at a point in time at which the polymer is still fully or substantially in dissolved form and no nanoparticles have yet formed. If the active compound precipitates before formation of the nanoparticles, it can no longer be enclosed in the polymer, so that nanoparticles in which little or no active compound at all is embedded are obtained in the course of the further evaporation.

With use of an organic solvent with which the greatest proportion of aqueous solvent can be admixed on successive admixing of aqueous solvent, the period in which the active compound is in solution during the evaporation can be extended and premature undesired precipitation of active compound can be prevented. Due to the extended period in which the active compound is in solution during the evaporation, the nanoparticles which simultaneously enclose some of the active compound preferentially form first. With advancing evaporation, the decreasing proportion of organic solvent in the mixture is no longer sufficient to keep the active compound in solution due to the co-solvent effect. Finally, the active compound which has not yet been encapsulated distributes itself in the hydrophobic core of the nanoparticles in this process.

According to an advantageous embodiment present invention, the organic solvent is determined by the following method:

(a) preparation of solutions of the active compound having the same proportion of active compound in each case in various organic solvents, (b) addition of an in each case identical amount of aqueous solution to each of the solutions prepared in step (a), (c) checking whether the active compound is in each case fully dissolved in the solutions of step (b), (d) repeated performance of steps (b) and (c) with the solutions in which the active compound is fully dissolved in step (c) until the active compound is no longer fully dissolved in step (c), (e) identification of the organic solvent with which the greatest amount of aqueous solution can be admixed cumulatively in step (d) before the active compound is no longer fully dissolved.

The present invention therefore also relates to an embodiment of the process which is characterised in that the organic solvent is determined by the following method:

(a) preparation of solutions of the active compound having the same proportion of active compound in each case in various organic solvents, (b) addition of an in each case identical amount of aqueous solution to each of the solutions prepared in step (a), (c) checking whether the active compound is in each case fully dissolved in the solutions of step (b), (d) repeated performance of steps (b) and (c) with the solutions in which the active compound is fully dissolved in step (c) until the active compound is no longer fully dissolved in step (c), (e) identification of the organic solvent with which the greatest amount of aqueous solution can be admixed cumulatively in step (d) before the active compound is no longer fully dissolved.

According to an advantageous embodiment of the invention, the method for determining the organic solvent is with the organic solvents methanol, ethanol, isopropanol, n-butanol, tert-butanol, acetone, dimethylformamide, tetrahydrofuran and dimethyl sulfoxide. The invention therefore also relates to an embodiment of the process according to the invention which is characterised in that the organic solvents employed are methanol, ethanol, isopropanol, n-butanol, tert-butanol, acetone, dimethylformamide, tetrahydrofuran and dimethyl sulfoxide.

If an excessively large amount of aqueous phase is employed in step (b) according to Claim 1 (mixing of the organic and aqueous phase), precipitation of the active compound may occur owing to the associated reduction of the solubility of active compound and polymer, where the active compound is then no longer available for embedding into the nanoparticles. According to an advantageous embodiment of the invention, the amount of aqueous phase is therefore selected so that, after mixing of the organic and aqueous phase in step (b) of Claim 1, the aqueous phase is present in an amount, in relation to the organic phase, which is below the maximum amount which can be admixed with the organic phase without the active compound no longer being fully dissolved. The invention therefore also relates to an embodiment of the process which is characterised in that the amount of aqueous phase is selected so that, after mixing of the organic and aqueous phase in step (b) of Claim 1, the aqueous phase is present in an amount, in relation to the organic phase, which is below the maximum amount which can be admixed with the organic phase without the active compound no longer being fully dissolved.

In order to ensure that the active compound is fully dissolved before commencement of the evaporation, it is sensible to select the amount of aqueous phase in relation to the organic phase in the method so that it is significantly below the maximum amount which can be admixed with the organic phase without the active compound no longer being fully dissolved. If, for example, a mixture of organic and aqueous phase results in precipitation of active compound from a volume ratio 3:2 v/v, organic and aqueous phase can be employed in the co-solvent evaporation, for example, in a volume ratio of 4:1 v/v, so that it is ensured that both components are fully dissolved.

It is preferred for the determination of the maximum amount of aqueous phase which can be admixed with the organic phase to be carried out in accordance with steps (a) to (d) of the method described on page 17 [page 16 of this English translation] for the determination of the organic solvent. The invention therefore also relates to an embodiment which is characterised in that the determination of the maximum amount of aqueous phase which can be admixed with the organic phase is carried out in accordance with steps (a) to (d) of the method described on page 17 [page 16 of this English translation] for the determination of the organic solvent.

The performance of the process according to the invention advantageously results in nanoparticles having increased active-compound loading and biphasic release of active compound, where, after administration, firstly rapid release of active compound (initial dose), which is followed by longer-lasting release of active compound. The invention therefore also relates to nanoparticles which are characterised in that they have been produced by the process according to the invention.

EXAMPLES

Example 1

Figure 1:
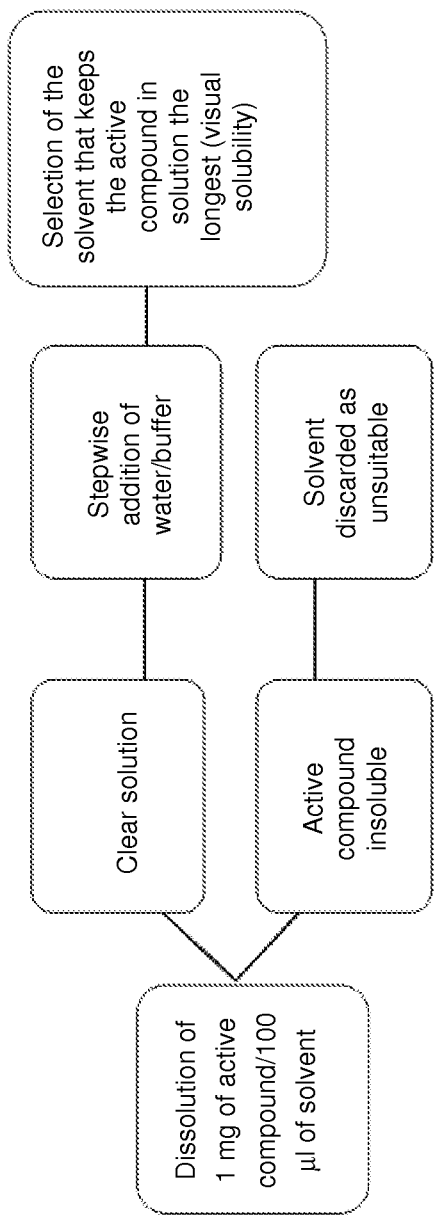
FIG. 1 is a diagrammatic representation of the procedure.
Figure 2:
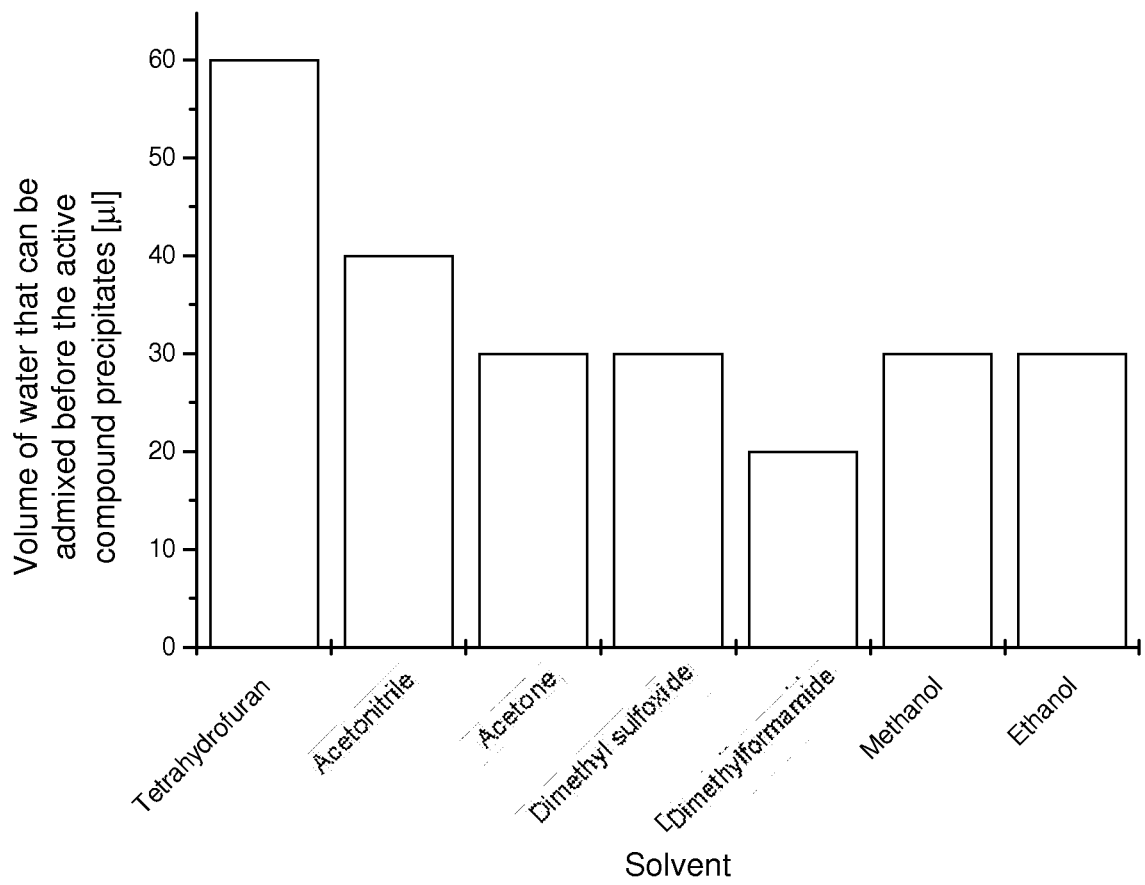
FIG. 2 shows the visual solubility of dexamethasone.
Figure 3:
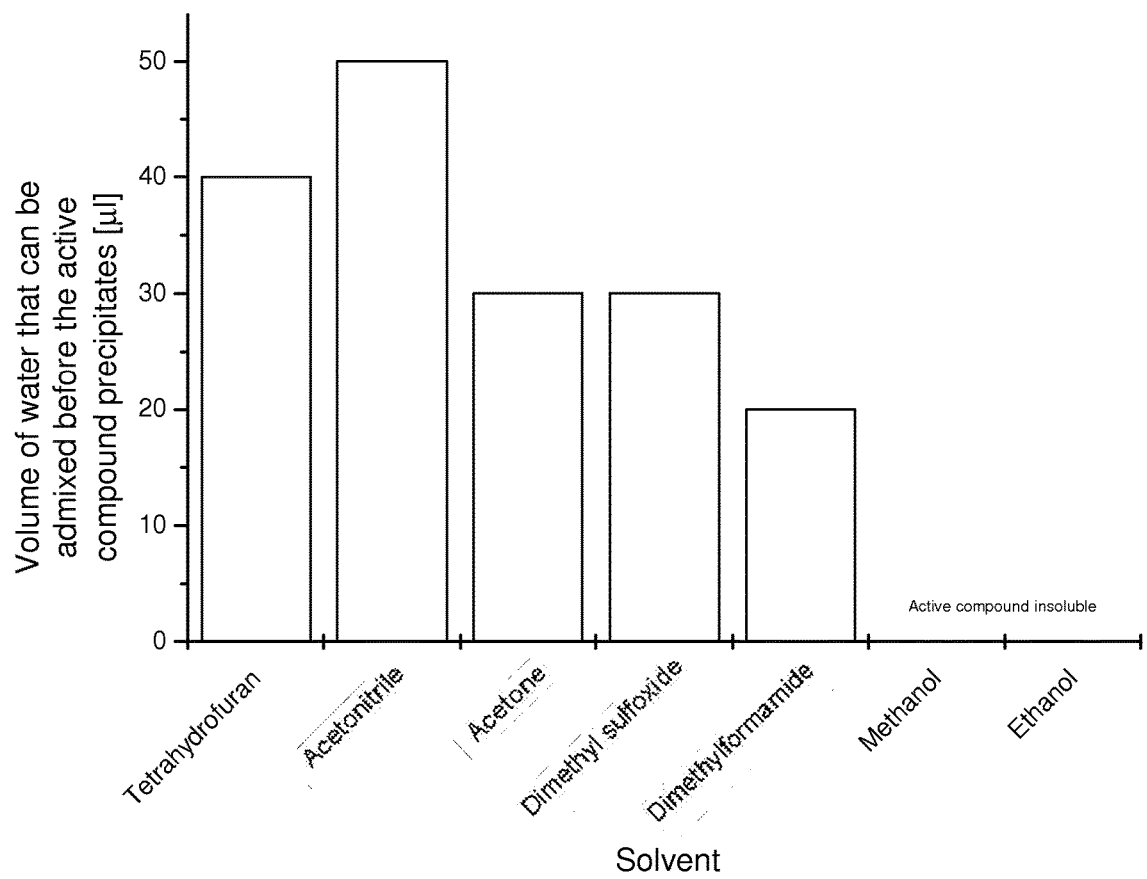
FIG. 3 shows the visual solubility of active compound B.
The examples, without being restricted thereto, explain the invention.

For loading experiments, the active compounds dexamethasone and 5-[2-(2-fluorophenyl)-1,8-naphthyridin-4-yl]-2,6-naphthyridin-1-ylamine (also called active compound B below) were used. For solvent selection, the active compounds were each dissolved in the following solvents with a concentration of 1 mg/100 µl: tetrahydrofuran (THF), acetonitrile (ACN), acetone, dimethyl sulfoxide (DMSO), dimethylformamide (DMF), methanol, ethanol. Additionally, 0.1% of trifluoroacetic acid (v/v) were added to each organic solution of active compound B in order to establish an apparent "pH". 10 µl of water were added successively to each of the solutions and mixed until the active compound began to precipitate (visual solubility). FIG. 2 shows the visual solubility of dexamethasone, FIG. 3 shows the visual solubility of active compound B.

For dexamethasone, owing to its increased visual solubility in tetrahydrofuran, this solvent was selected as organic solvent for the production of the nanoparticles. 4:1 v/v (THF:water) was fixed as the starting ratio.

For active compound B, owing to its increased visual solubility in, this solvent was selected as organic solvent for the production of the nanoparticles. 5:1 v/v (ACN:water) was fixed as the starting ratio.

Example 2

The following polymers were used for the production and loading of nanoparticles: PEG-PDLLA [5-b-23], PEG-PCL [5-b-32.5], PEG-PVPy [5-b-20] from Polymersource Inc., Montreal, Canada. Furthermore, PEG-PLGA [5-b-28] (Resomer RGP 50155 d) from Boehringer Ingelheim, Ingelheim, Germany, was used. All polymers were in research quality.

In order to be able to compare the other production processes with co-solvent evaporation and the encapsulation in various polymers with one another, the nanoparticles were produced as follows and loaded with dexamethasone:

Direct dialysis from acetone:

10 mg or 20 mg of block copolymer and 1 mg or 2 mg respectively of dexamethasone were dissolved in 1 ml of acetone. This solution was introduced into a dialysis tube (MWCO 6-8 kDa, Spectrumlabs Inc., Breda, The Netherlands) and sealed. The dialysis was carried out against 5 l of water for 24 h; the water was replaced once after 4 h. The formulation formed was subsequently removed from the dialysis tube, passed through a 0.2 µm filter and adjusted to a volume of 2 ml.

O/W Emulsion:

Pre-shaped micelles without active compound were firstly produced as described under 2.a. "Direct dialysis". For the active-compound loading, 2 mg of dexamethasone were dissolved in 1 ml of dichloromethane (VWR, Darmstadt, Germany). This organic solution was injected into 5 ml of the aqueous micellar phase with constant stirring. An O/W emulsion was formed, which was stirred further at room temperature overnight. The filtration step through a 0.2 µm filter and the volume adaptation to 5 ml was subsequently carried out.

Co-Solvent Evaporation with Subsequent Dialysis:

10 mg of block copolymer and 2 mg of dexamethasone were dissolved in 6 ml of THF. 2 ml of water were added to this solution. This solution was evaporated in a round-bottomed flask at a temperature of at 25° C. and a pressure of 30 mbar for 10 min. The formulation obtained was introduced into a Float-A-Lyzer G2 dialysis tube (MWCO 8-10 kDa, Spectrumlabs Inc., Berda, The Netherlands), which, in the case of the subsequent dialysis, had been preequilibrated against saturated solution in dexamethasone-saturated water. The formulation was then dialysed against 5 l of water or dexamethasone-saturated water for 24 h. Finally, the formulation was passed through a 0.2 µm filter, and the volume was adjusted to 2 ml.

The nanoparticles produced by the various processes were characterised with respect to their active-compound loading and particle sizes and the size distributions thereof.

Determination of the Active-Compound Loading Via HPLC

100 µl of the resultant micellar formulation were dissolved in 900 µl of acetonitrile. This solution was detected using an HPLC system (Merck Hitachi La Chrom Elite) via a UV detector (detection wavelength: 282 nm). The separation was carried out on an Agilent Eclipse Plus C18 column (particle size 3.5 µm, length 5 cm) at 30° C. A gradient method was utilised for the separation. The mobile phase A here consisted of 90% of acetonitrile and 10% of ammonium acetate buffer pH 4.5 (v/v), the mobile phase B had the reverse composition. The dexamethasone sample concentration was determined via a calibration curve.

The calculation of the active-compound loading was carried out via formula 1 below:

$$\text{active compound loading}[\%] = \frac{\text{active compound concentration}\left[\frac{mg}{ml}\right]}{\text{polymer concentration}\left[\frac{mg}{ml}\right]} \cdot 100\% \quad (1)$$

Particle Size Determination by Means of Dynamic Light Scattering (DLS)

The DLS technique determines the hydrodynamic particle radius or diameter. For this purpose, the samples are diluted 1:100 (v/v) with water and measured in a Malvern Zetasizer Nano ZS (Malvern Instruments Ltd., Worcestershire, UK) in back-scatter mode. Particle sizes were calculated via cumulate analysis. In addition, the polydispersity index (PdI) was calculated, which is regarded as a measure of the scattering of the particle-size distribution. The PdI can have values between 0 and 1 where 0 denotes monodisperse and 1 denotes (fully) polydisperse.

The results are compiled in the following Table 1.

| Polymer | Polymer concentration [%] w/v | compound/polymer ratio initial | Production method | Solvent and conditions | Active compound loading [%] | dynamic particle size [nm] | PdI |
|---|---|---|---|---|---|---|---|
| PEG-PDLLA [5-b-23] | 0.5 | 1:5 | Co-solv. evaporation | THF, dialysis against water | <LOQ | 50.41 ± 2.47 | 0.120 ± 0.047 |
| PEG-PDLLA [5-b-23] | 0.5 | 1:5 | Co-solv. evaporation | THF, dialysis against active-compound-saturated soln. | 1.56 ± 0.24 | 61.43 ± 1.39 | 0.102 ± 0.006 |
| PEG-PLGA [5-b-28] | 0.5 | 1:5 | Co-solv. evaporation | THF, dialysis against water | <LOQ | 62.67 ± 1.60 | 0.091 ± 0.014 |
| PEG-PLGA [5-b-28] | 0.5 | 1:5 | Co-solv. evaporation | THF, dialysis against active-compound-saturated soln. | 1.19 ± 0.13 | 69.18 ± 1.23 | 0.057 ± 0.026 |
| PEG-PCL [5-b-32.5] | 0.5 | 1:5 | Co-solv. evaporation | THF, dialysis against water | <LOQ | 80.59 ± 2.98 | 0.093 ± 0.053 |
| PEG-PCL [5-b-32.5] | 0.5 | 1:5 | Co-solv. evaporation | THF, dialysis against active-compound-saturated soln. | 1.39 ± 0.36 | 87.69 ± 2.70 | 0.126 ± 0.034 |
| PEG-PVPy [5-b-20] | 0.5 | 1:5 | Co-solv. evaporation | THF, dialysis against water | 10.74 ± 1.8 | 33.97 ± 1.50 | 0.204 ± 0.016 |
| PEG-PVPy [5-b-20] | 0.5 | 1:5 | Co-solv. evaporation | THF, dialysis against active-compound-saturated soln. | 18.67 ± 0.21 | 36.73 ± 0.95 | 0.213 ± 0.006 |
| PEG-PVPy [5-b-20] | 1.0 | 1:5 | Co-solv. evaporation | THF, dialysis against active-compound-saturated soln. | 19.25 ± 0.54 | 52.13 ± 1.34 | 0.258 ± 0.011 |
| PEG-PVPy [5-b-20] | 0.5 | 1:5 | Co-solv. evaporation | Acetone, dialysis against active-compound-saturated soln. | 12.07 ± 1.21 | 41.09 ± 2.80 | 0.136 ± 0.011 |
| PEG-PVPy [5-b-20] | 1.0 | 1:5 | Co-solv. evaporation | Acetone, dialysis against active-compound-saturated soln. | 10.84 ± 2.64 | 44.73 ± 4.65 | 0.118 ± 0.011 |
| PEG-PVPy [5-b-20] | 0.5 | 1:10 | Direct dialysis | Acetone | 1.71 ± 0.15 | 56.42 ± 7.29 | 0.178 ± 0.056 |
| PEG-PVPy [5-b-20] | 1.0 | 1:5 | Direct dialysis | Acetone | 0.62 ± 0.60 | 66.91 ± 2.29 | 0.162 ± 0.011 |
| PEG-PVPy [5-b-20] | 0.5 | 1:10 | O/W emulsion | Dichloromethane, prefabricated particles from acetone | 8.74 ± 0.03 | 52.42 ± 2.00 | 0.150 ± 0.012 |

-continued

| Polymer | Polymer concentration [%] w/v | compound/polymer ratio initial | Production method | Solvent and conditions | Active compound loading [%] | dynamic particle size [nm] | PdI |
|---|---|---|---|---|---|---|---|
| PEG-PVPy [5-b-20] | 1.0 | 1:10 | O/W emulsion | Dichloromethane, prefabricated particles from acetone | 7.81 ± 0.18 | 68.92 ± 3.53 | 0.185 ± 0.036 |
| PEG-PVPy [5-b-20] | 0.5 | 2:5 | O/W emulsion | Dichloromethane, prefabricated particles from acetone | 13.50 ± 5.05 | 52.19 ± 0.67 | 0.186 ± 0.022 |

Table 1, in which PEG-PDLLA denotes pegylated poly(D,L-lactic acid), PEG-PLGA denotes pegylated poly(lactic acid-co-glycolic acid), PEG-PCL denotes pegylated poly(caprolactone), PEG-PVPy denotes pegylated poly-4-(vinylpyridine), LOQ denotes limit of quantification (determination limit of the HPLC method), co-solv. evaporation denotes co-solvent evaporation and THF denotes tetrahydrofuran.

Example 3

Production and Loading of Nanoparticles Laden with Active Compound B

The production and loading of the nanoparticles was carried out by the process described in this invention as a combination between co-solvent evaporation and dialysis against active-compound-saturated solution.

10 mg of block copolymer and 1 mg of active compound were dissolved in 8 ml of acetonitrile/0.1% of trifluoroacetic acid (v/v) with ultrasound treatment. The solution obtained was mixed with 2 ml of water. The mixture was subsequently introduced into a round-bottomed flask, and the organic solvent was evaporated under reduced pressure (30 mbar) and at 25° C. (10 min). The nanoparticles obtained were introduced into a Float-A-Lyzer G2 dialysis tube (MWCO 8-10 kDa, Spectrumlabs Inc., Berda, The Netherlands) and dialysed for 24 h against 5 l of phosphate-buffered saline solution (PBS buffer), pH 7.4, saturated with active compound B. Finally, the formulation was passed through a 0.2 μm filter, and the volume of the formulation was adjusted to 2 ml.

Determination of the Active-Compound Loading

100 μl of the formulation obtained were dissolved in 900 μl of acetonitrile. This solution was detected using an HPLC system (Merck Hitachi La Chrom Elite) via a UV detector (detection wavelength: 254 nm). The separation was carried out on an Agilent Eclipse Plus C18 column (particle size 3.5 μm, length 5 cm) at 30° C. A gradient method was utilised for the separation. The mobile phase A here consisted of 90% of acetonitrile and 10% of water with 0.1% of trifluoroacetic acid (v/v), the mobile phase B had the reverse composition. The active compound B sample concentration was determined via a calibration curve.

The calculation of the active-compound loading was carried out here in accordance with formula 1. Particle sizes and size distributions were determined analogously to Example 2.

The results with the optimum loading technique on use of various block copolymers are summarized in Table 2.

| Polymer | Polymer concentration [%] w/v | compound/polymer ratio initial | Production method | Solvent and conditions | Active compound loading [%] | particle size [nm] | PdI |
|---|---|---|---|---|---|---|---|
| PEG-PDLLA [5-b-23] | 0.5 | 1:10 | Co-solv. evaporation | ACN/0.1% TFA, dialysis with saturation | <LOQ | n.a. | n.a. |
| PEG-PLGA [5-b-28] | 0.5 | 1:10 | Co-solv. evaporation | ACN/0.1% TFA, dialysis with saturation | 25.4 | n.a. | n.a. |
| PEG-PCL [5-b-32.5] | 0.5 | 1:10 | Co-solv. evaporation | ACN/0.1% TFA, dialysis with saturation | 24.9 | n.a. | n.a. |
| PEG-PVPy [5-b-20] | 0.5 | 1:10 | Co-solv. evaporation | ACN/0.1% TFA, dialysis with saturation | 40.6 | n.a. | n.a. |
| PEG-PLGA [5-b-28] | 5.0 | 1:10 | Co-solv. evaporation | ACN/0.1% TFA, dialysis with saturation | 101.90 ± 6.44 | 122 | 0.183 |

Table 2, in which PEG-PDLLA denotes pegylated poly(D,L-lactic acid), PEG-PLGA denotes pegylated poly(lactic acid-co-glycolic acid), PEG-PCL denotes pegylated poly(caprolactone), PEG-PVPy denotes pegylated poly-4-(vinylpyridine), LOQ denotes limit of quantification (determination limit of the HPLC method), co-solv. evaporation denotes co-solvent evaporation, ACN denotes acetonitrile and TFA denotes trifluoroacetic acid.

The invention claimed is:

1. Process for the production of nanoparticles comprising the steps of
   (a) dissolution of at least one active compound and at least one polymer in an organic solvent,
   (b) mixing of the solution prepared in step (a) with an aqueous phase,
   (c) evaporation of the organic solvent,
   (d) purification of the nanoparticles laden with active compound obtained in step (c) by means of dialysis against aqueous dialysis solution comprising the same active compound.

2. Process according to claim 1, characterised in that the active compound has a saturation solubility in water <200 µg/ml, measured at 25° C.

3. Process according to claim 2, characterised in that the active compound used is an active compound which is selected from the group consisting of chemotherapeutic agents, antirheumatics, anti-infective agents, antimycotic agents, lipid-lowering agents, antioxidants and vitamins, such as, for example, tocopherol derivatives, retinoic acid derivatives, cholecalciferol, antibiotics, cholesterol and fatty acids.

4. Process according to claim 1, characterised in that the polymer employed is an amphiphilic polymer.

5. Process according to claim 4, characterised in that the polymer employed is a block copolymer.

6. Process according to claim 4, characterised in that the block copolymer contains as hydrophilic component: polyethylene glycol, polypropylene glycol, polybutylene glycol, polyacrylamide, polyvinyl alcohol, polysaccharide or a copolymer thereof, and as hydrophobic component: polylactic acid, polyglycolic acid, polyhydroxybutyric acid, polyhydroxyvaleric acid or a copolymer thereof, and as an additional component polyacrylic acid and derivatives thereof, or polysiloxane and derivatives thereof.

7. Process according to claim 6, characterised in that the block copolymer employed is polyethylene glycol-polylactic acid, polyethylene glycol-polyglycolic acid, polyethylene glycol-polylactic acid-co-glycolic acid, polyethylene glycol-polyhydroxyvaleric acid, polyethylene glycol-polysiloxane, polyethylene glycol-polysiloxane-co-acrylic acid, polyethylene glycol-polymethylmethacrylic acid, polyethylene glycol-polymethylethacrylic acid, polyethylene glycol-polyisoprylacrylic acid or polyethylene glycol-polystyrene.

8. Process according to claim 1, characterised in that the organic solvent used is a solvent which is at least partially miscible with water.

9. Process according to claim 8, characterised in that the organic solvent employed is methanol, ethanol, isopropanol, n-butanol or tert-butanol, acetone, dimethylformamide, tetrahydrofuran or dimethyl sulfoxide.

10. Process according to claim 1, characterised in that, in step (a) according to claim 1, an acid or base is dissolved in the organic solvent besides polymer and active compound, and/or in that an acid or base is dissolved in the aqueous solvent in step (b) of claim 1.

11. Process according to claim 10, characterised in that the acid is formic acid, acetic acid, trifluoroacetic acid, hydrochloric acid, nitric acid or sulfuric acid, and the base is dimethylamine or trimethylamine, sodium hydroxide, potassium hydroxide or ammonia.

12. Process according to claim 1, characterised in that the organic solvent used in the production of the nanoparticles in step (a) of claim 1 is the organic solvent with which the greatest proportion of aqueous solvent can be admixed without active compound precipitating out of the solution during preparation of a solution comprising the active compound in defined amount compared with solutions comprising this active compound in the same amount in each case in other organic solvents on successive admixing of aqueous solvent.

13. Process according to claim 12, characterised in that the organic solvent is determined by the following method:
   (a) preparation of solutions of the active compound having the same proportion of active compound in each case in various organic solvents,
   (b) addition of an in each case identical amount of aqueous solution to each of the solutions prepared in step (a),
   (c) checking whether the active compound is in each case fully dissolved in the solutions of step (b),
   (d) repeated performance of steps (b) and (c) with the solutions in which the active compound is fully dissolved in step (c), until the active compound is no longer fully dissolved in step (c),
   (e) identification of the organic solvent with which the greatest amount of aqueous solution can be admixed cumulatively in step (d) before the active compound is no longer fully dissolved.

14. Process according to claim 12, characterised in that the organic solvents employed are methanol, ethanol, isopropanol, n-butanol, tert-butanol, acetone, dimethylformamide, tetrahydrofuran and dimethyl sulfoxide.

15. Process according to claim 1, characterised in that the amount of aqueous phase is selected so that, after mixing of the solution of organic solvent and aqueous phase in step (b), the aqueous phase is present in an amount, in relation to the organic solvent, which is below the maximum amount which can be admixed with the organic solvent without the active compound no longer being fully dissolved.

16. Process according to claim 15, characterised in that the determination of the maximum amount of aqueous phase which can be admixed with the solution of organic solvent is carried out in accordance with steps (a) to (d)
   (a) preparation of solutions of the active compound having the same proportion of active compound in each case in various organic solvents,
   (b) addition of in each case an identical amount of aqueous solution to each of the solutions prepared in step (a),
   (c) checking whether the active compound is in each case fully dissolved in the solutions of step (b),
   (d) repeated performance of steps (b) and (c) with the solutions in which the active compound is fully dissolved in step (c), until the active compound is no longer fully dissolved in step (c).

17. Nanoparticles, produced by the process according to claim 1.

18. Process according to claim 1, characterized in that the active compound has a saturation solubility <100 µg/ml, measured at 25° C.

19. Process according to claim 2, characterized in that the active compound used is selected from the group consisting of taxol derivatives, camptothecin derivatives, platinum complexes or N-mustard compounds, dexamethasone, mometasone, beclomethasone, prednisolone, ritonavir, ketoconazole, itraconazole, griseofulvin, fenofibrate, tocopherol derivatives, retinoic acid derivatives, cholecalciferol, vancomycin or teicomycin.

20. Process according to claim 4, characterized in that the block copolymer contains as hydrophilic component: polyethylene glycol-polypropylene glycol copolymer, polyethylene glycol-polypropylene glycol-polyethylene glycol copolymer, and as hydrophobic component: polylactic-co-glycolic acid, and as an additional component hydroxypropylethylacrylic acid, or hydroxypropylmethylacrylic acid, or polysiloxane and derivatives thereof.

* * * * *